(12) United States Patent
DeAngelis et al.

(10) Patent No.: US 11,937,979 B2
(45) Date of Patent: Mar. 26, 2024

(54) ULTRASONIC TRANSDUCERS, WIRE BONDING MACHINES INCLUDING ULTRASONIC TRANSDUCERS, AND RELATED METHODS

(71) Applicant: Kulicke and Soffa Industries, Inc., Fort Washington, PA (US)

(72) Inventors: Dominick Albert DeAngelis, Villanova, PA (US); Gary Walter Schulze, Bethlehem, PA (US)

(73) Assignee: Kulicke and Soffa Industries, Inc., Fort Washington, PA (US)

( * ) Notice: Subject to any disclaimer, the term of this patent is extended or adjusted under 35 U.S.C. 154(b) by 240 days.

(21) Appl. No.: 17/718,474

(22) Filed: Apr. 12, 2022

(65) Prior Publication Data

US 2022/0338838 A1     Oct. 27, 2022

Related U.S. Application Data

(60) Provisional application No. 63/180,480, filed on Apr. 27, 2021.

(51) Int. Cl.
*B23K 20/00* (2006.01)
*A61B 8/00* (2006.01)
*B23K 20/10* (2006.01)

(52) U.S. Cl.
CPC ............ *A61B 8/445* (2013.01); *A61B 8/4433* (2013.01); *A61B 8/4455* (2013.01); *A61B 8/4494* (2013.01); *B23K 20/005* (2013.01); *B23K 20/10* (2013.01)

(58) Field of Classification Search
CPC .. B23K 20/005; B23K 20/004; B23K 20/007; B23K 2101/42; B23K 20/106; A61B 8/445; A61B 8/4433; A61B 8/4455; A61B 8/4494; H01L 2224/78308; H01L 2224/78309; H01L 2224/78349; H01L 2924/00014; H01L 24/78; B06B 1/06; B06B 2201/72; B29C 65/08–088
USPC .................... 228/1.1, 110.1, 180.5, 4.5, 904; 156/73.1–73.6, 580.1–580.2
See application file for complete search history.

(56) References Cited

U.S. PATENT DOCUMENTS

| | | | |
|---|---|---|---|
| 5,180,093 A * | 1/1993 | Stansbury | B23K 20/106 228/55 |
| 5,469,011 A * | 11/1995 | Safabakhsh | B23K 20/106 228/1.1 |
| 5,595,328 A | 1/1997 | Safabakhsh et al. | |
| 5,603,445 A * | 2/1997 | Hill | B06B 3/00 228/904 |
| 5,699,953 A | 12/1997 | Safabakhsh | |

(Continued)

FOREIGN PATENT DOCUMENTS

| | | | | |
|---|---|---|---|---|
| CN | 101777506 A | * | 7/2010 | ............. H01L 24/78 |
| CN | 102186620 A | * | 9/2011 | ........... B23K 20/002 |

(Continued)

*Primary Examiner* — Kiley S Stoner
(74) *Attorney, Agent, or Firm* — Christopher M. Spletzer, Sr.

(57) ABSTRACT

An ultrasonic transducer system is provided. The ultrasonic transducer system includes a transducer body, wherein at least a portion of a surface of the transducer body includes a processed area. The processed area has a changed condition at the surface of the transducer body.

18 Claims, 7 Drawing Sheets

(56) References Cited

U.S. PATENT DOCUMENTS

| | | | |
|---|---|---|---|
| 5,829,663 A * | 11/1998 | Khelemsky | H01L 24/78 228/904 |
| 5,884,834 A | 3/1999 | Vinson et al. | |
| 7,137,543 B2 | 11/2006 | DeAngelis et al. | |
| 7,462,960 B2 * | 12/2008 | Or | B23K 20/106 310/26 |
| 8,251,275 B2 | 8/2012 | DeAngelis et al. | |
| 9,136,240 B2 | 9/2015 | Chylak et al. | |
| 10,381,321 B2 | 8/2019 | DeAngelis | |
| 2017/0005064 A1 * | 1/2017 | Sugito | B23K 20/005 |
| 2017/0005065 A1 * | 1/2017 | Sugito | B23K 20/106 |
| 2022/0187353 A1 * | 6/2022 | DeAngelis | H01L 24/78 |

FOREIGN PATENT DOCUMENTS

| | | | | |
|---|---|---|---|---|
| CN | 108273717 A | * | 7/2018 | B06B 1/06 |
| CN | 109982831 A | * | 7/2019 | B29C 65/08 |
| CN | 111822735 A | * | 10/2020 | B06B 1/06 |
| CN | 111844215 A | * | 10/2020 | B06B 1/06 |
| JP | H05245440 A | * | 9/1993 | |
| JP | H1064942 A | * | 6/1998 | |
| JP | 2001291747 A | * | 10/2001 | B23K 20/005 |
| JP | 3566678 B2 | * | 9/2004 | H01L 24/78 |
| JP | 2005212045 A | * | 8/2005 | B23B 27/007 |
| JP | 4049608 B2 | * | 2/2008 | H01L 24/78 |
| JP | 6592632 B1 | * | 10/2019 | A61F 13/15 |
| KR | 20140140979 A | * | 12/2014 | |
| KR | 102111584 B1 | * | 5/2020 | |
| WO | WO-2014103463 A1 | * | 7/2014 | B23K 20/007 |

\* cited by examiner

ULTRASONIC TRANSDUCERS, WIRE BONDING MACHINES INCLUDING ULTRASONIC TRANSDUCERS, AND RELATED METHODS

CROSS-REFERENCE TO RELATED APPLICATION

This application claims the benefit of U.S. Provisional Application No. 63/180,480, filed Apr. 27, 2021, the content of which is incorporated herein by reference.

FIELD

The invention relates to ultrasonic transducers, and more particularly, to improved ultrasonic transducers, as well as wire bonding machines including such ultrasonic transducers, and related methods.

BACKGROUND

Ultrasonic transducers are used in various applications. For example, such ultrasonic transducers are widely used in semiconductor packaging equipment such as automatic wire bonding machines (e.g., ball bonding machines, wedge bonding machines, ribbon bonding machines, etc.) and advanced packaging machines (e.g., flip chip bonding machines such as thermocompression bonding machines, etc.).

In connection with wire bonding machines, ultrasonic bonding energy is typically applied to form wire bonds using an ultrasonic transducer. A wire bonding tool is attached to the transducer. The transducer typically includes a driver such as a stack of piezoelectric elements (e.g., piezoelectric crystals, piezoelectric ceramics, etc.). Electrical energy is applied to the driver, and converts the electrical energy to mechanical energy, thereby moving a tip of the wire bonding tool in a scrubbing motion to form wire bonds.

U.S. Pat. No. 5,595,328 (titled "SELF ISOLATING ULTRASONIC TRANSDUCER"); U.S. Pat. No. 5,699,953 (titled "MULTI RESONANCE UNIBODY ULTRASONIC TRANSDUCER"); U.S. Pat. No. 5,884,834 (titled "MULTI-FREQUENCY ULTRASONIC WIRE BONDER AND METHOD"); U.S. Pat. No. 7,137,543 (titled "INTEGRATED FLEXURE MOUNT SCHEME FOR DYNAMIC ISOLATION OF ULTRASONIC TRANSDUCERS"); U.S. Pat. No. 8,251,275 (titled "ULTRASONIC TRANSDUCERS FOR WIRE BONDING AND METHODS OF FORMING WIRE BONDS USING ULTRASONIC TRANSDUCERS"); U.S. Pat. No. 9,136,240 (titled "SYSTEMS AND METHODS FOR BONDING SEMICONDUCTOR ELEMENTS"); and U.S. Pat. No. 10,381,321 (titled "ULTRASONIC TRANSDUCER SYSTEMS INCLUDING TUNED RESONATORS, EQUIPMENT INCLUDING SUCH SYSTEMS, AND METHODS OF PROVIDING THE SAME") relate to ultrasonic transducers and are herein incorporated by reference in their entirety.

Conventional ultrasonic transducers, including those used in connection with wire bonding, suffer from a number of deficiencies. Thus, it would be desirable to provide improved ultrasonic transducers, wire bonding machines, and related methods.

SUMMARY

According to an exemplary embodiment of the invention, an ultrasonic transducer is provided. The ultrasonic transducer includes a transducer body, wherein at least a portion of a surface of the transducer body includes a processed area. The processed area has a changed condition at the surface of the transducer body.

According to another exemplary embodiment of the invention, a wire bonding machine is provided. The wire bonding machine includes a bond head assembly, and an ultrasonic transducer carried by the bond head assembly. The ultrasonic transducer includes a transducer body, wherein at least a portion of a surface of the transducer body includes a processed area. The processed area has a changed condition at the surface of the transducer body.

According to yet another exemplary embodiment of the invention, a method of providing an ultrasonic transducer is provided. The method includes the steps of: (a) providing a transducer body; and (b) processing at least a portion of a surface of the transducer body to produce a processed area having a changed condition at the surface of the transducer body.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION

According to various exemplary embodiments of the invention, areas of ultrasonic transducers (e.g., titanium transducers) are processed (e.g., coated) to reduce relative sliding wear from the static and/or dynamic interaction between (i) an integral tool clamp of the ultrasonic transducer and (ii) a work tool (e.g., a wire bonding tool).

For example, to reduce wear between an integral tool clamp of the ultrasonic transducer and the work tool (e.g., a replaceable wire bonding tool), processing (e.g., coating) is performed on at least a portion of the surface of the ultrasonic transducer to reduce friction (e.g., to reduce galling) and/or to increase surface hardness, with an objective of increasing the lifetime of ultrasonic transducers.

For example, a coating applied to a surface of the ultrasonic transducer may be a thin, durable intermediate layer (e.g., having a thickness between 1 μm and 5 μm) between (i) the body of the ultrasonic transducer and (ii) the work tool. The body of the ultrasonic transducer may be formed of a relatively soft material (e.g., titanium) which may be prone to galling, where such material may have a hardness on the order of HRC36. The work tool may be, for example, a wire bonding tool formed of a relatively hard material (e.g., alumina, zirconia toughened alumina, etc.) that may have a hardness on the order of HRC90.

In exemplary embodiments of the invention where a coating is applied to a surface of an ultrasonic transducer to act as a galling inhibitor, the wear reduction may be achieved primarily from reduced friction. In exemplary embodiments of the invention where a coating is applied to a surface of an ultrasonic transducer to act as a surface hardener, the reduction in wear may be achieved through the relative hardness ratio of the coating and the tool (e.g., harder coatings tend to result in less wear).

In examples where a hardness of the applied coating exceeds the work tool hardness (e.g., coating greater than HRC90 of alumina), the inexpensive replaceable work tool (e.g., a wire bonding tool) may tend to be the wear component instead of the expensive ultrasonic transducer (e.g., a titanium ultrasonic transducer), thus greatly improving the lifetime and performance of the transducer.

Examples of coatings that may be applied to at least a portion of a surface of a transducer body of an ultrasonic transducer include at least one of titanium nitride (TiN), diamond-like carbon (DLC), flash chrome, tungsten disulfide, titanium aluminum nitride, and composite diamond coating (CDC). An exemplary thickness of such an applied coating may be between 1 μm and 5 μm, between 1 μm and 10 μm, among others. A particular coating may be selected at least in part, for example, based on how well it adheres to the material of the transducer body (e.g., titanium).

The processed area of the transducer body (e.g., a coated area of the surface of the transducer body) may be altered after processing in accordance with the invention. For example, in applications where a coating is applied to the transducer body, the coating may be machined or otherwise varied, as desired, in the specific application (e.g., to maintain desired tolerances, etc.).

According to various exemplary embodiments of the invention, ultrasonic transducers are provided which include a transducer body. At least a portion of a surface of the transducer body includes a processed area. The processed area has a changed condition (e.g., wherein the changed condition may be configured to reduce galling and/or to reduce wear at the processed area). The processed area may include an exterior surface of the transducer body (e.g., the entire exterior surface, or substantially the entire exterior surface). However, the processed area may also include specific targeted areas of the surface such as, for example: an area of the transducer body defining an aperture configured to receive a wire bonding tool; and an area of the transducer body defining another aperture (sometimes referred to herein as a second aperture configured to receive a fastener for tightening the aforementioned aperture during engagement with the wire bonding tool).

As referenced above, the changed condition may include a coating applied at the processed area. Another example of a changed condition includes a passivated condition at the processed area (e.g., wherein the passivated condition includes an anodized condition). Other examples of changed conditions are contemplated.

In accordance with certain exemplary aspects of the invention, the processed area has (i) a coefficient of friction of less than 0.2, and/or (ii) a hardness greater than 90 HRC.

Figure 1A:
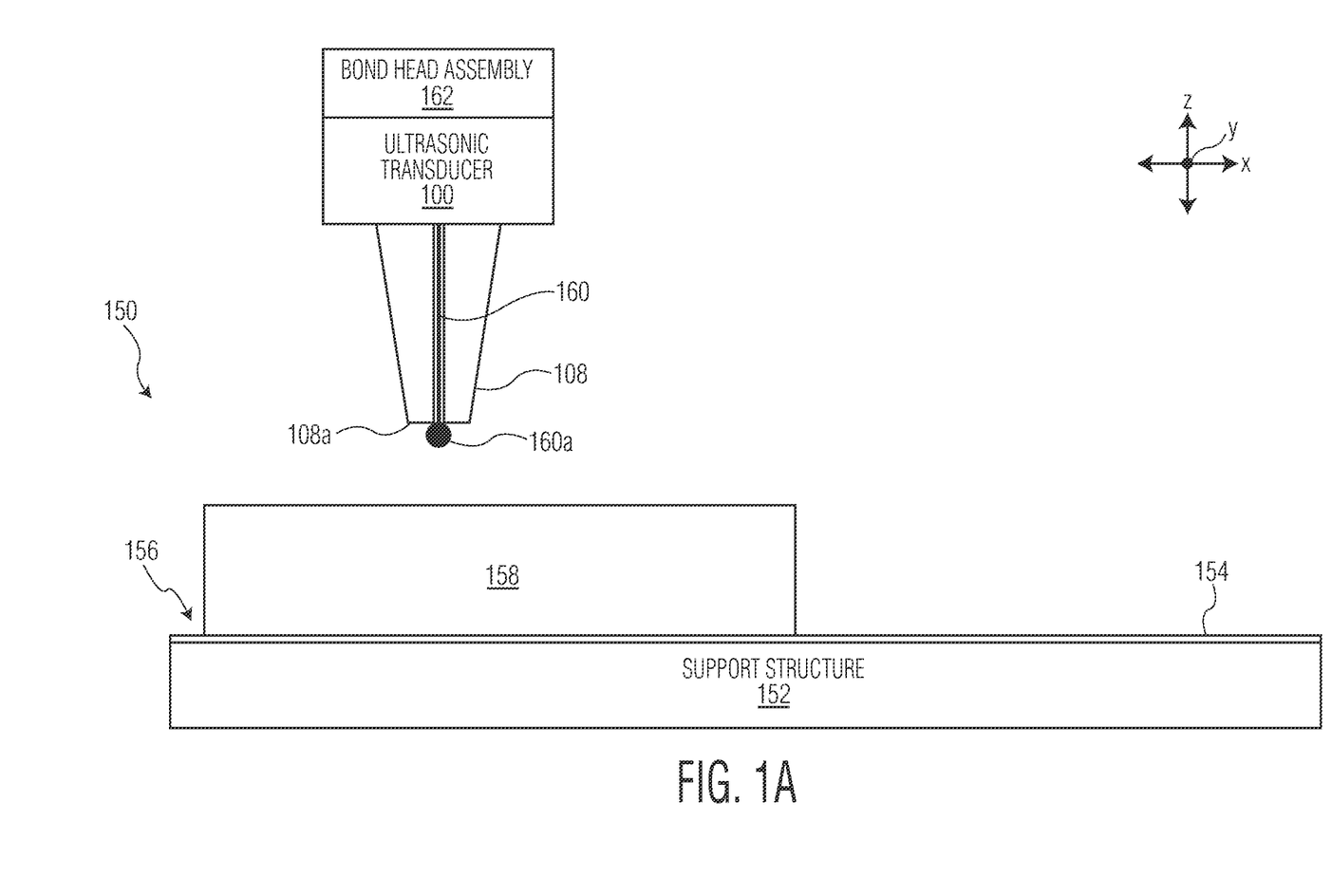
FIG. 1A is a side sectional block diagram view of a wire bonding machine in accordance with an exemplary embodiment of the invention.
Figure 1B:
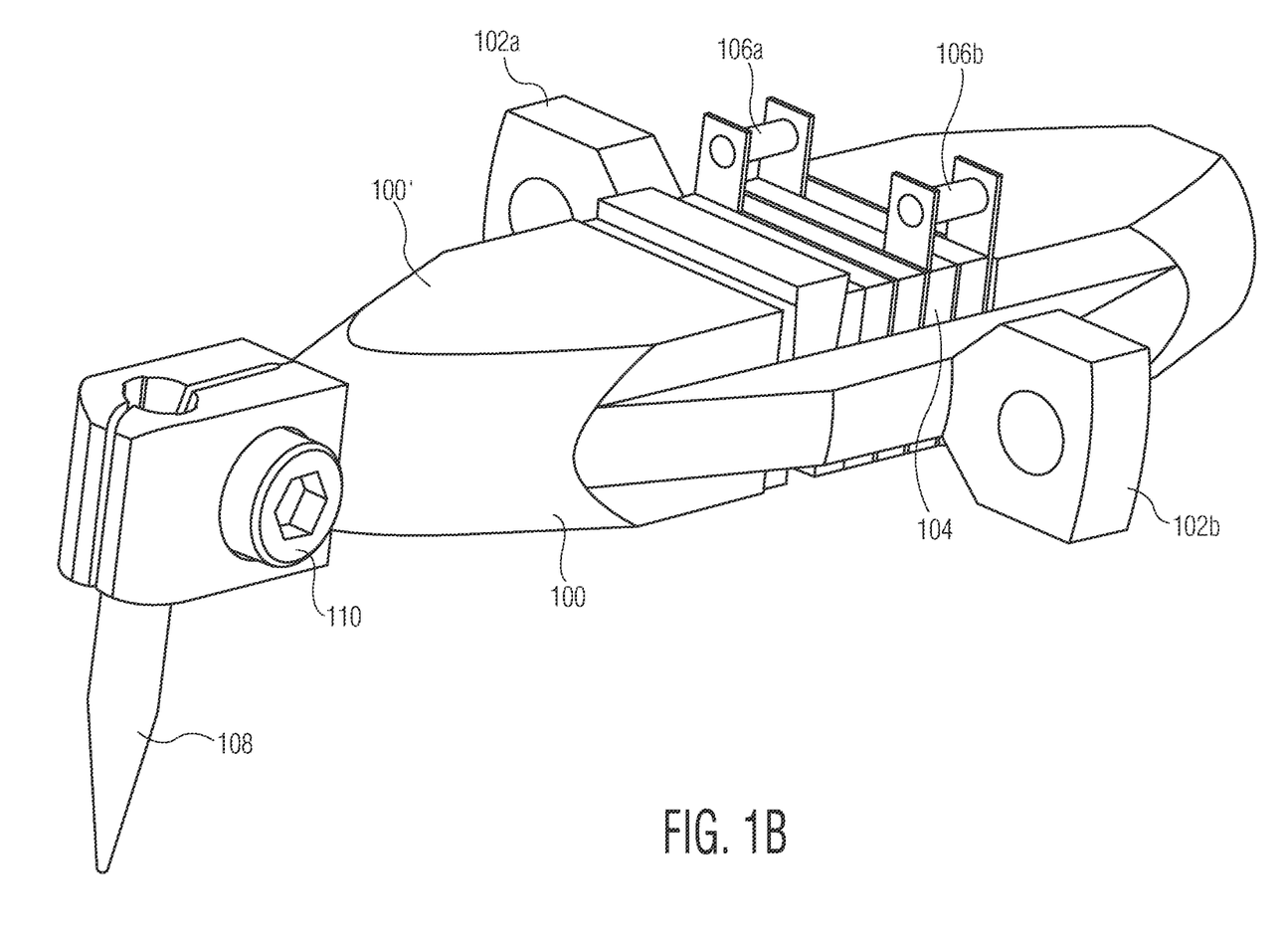
FIG. 1B is a perspective view of an ultrasonic transducer in accordance with an exemplary embodiment of the invention.
Figure 1C:
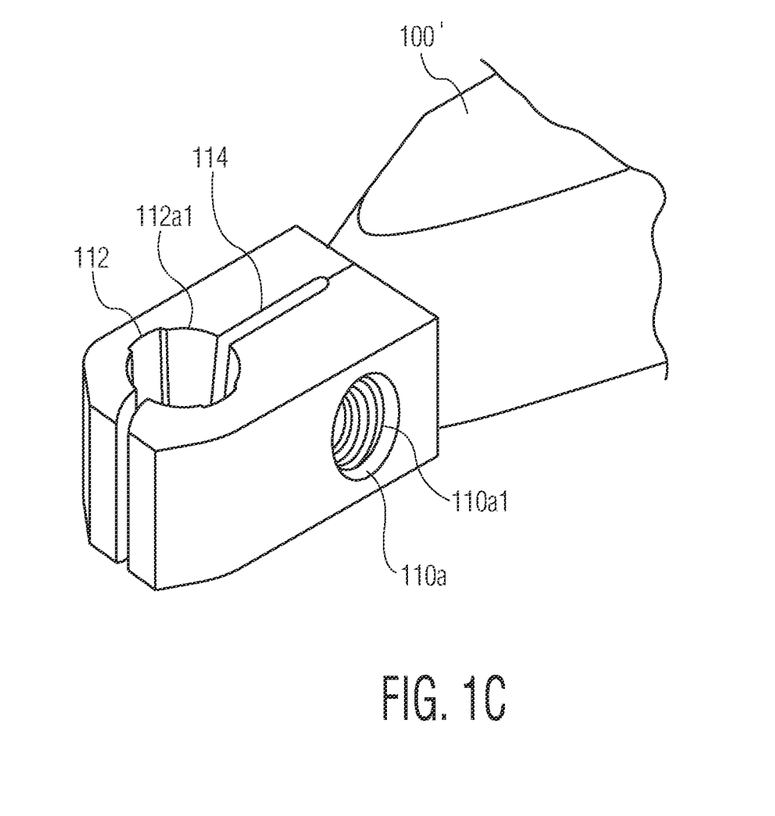
FIG. 1C is a perspective view of a portion of the ultrasonic transducer of FIG. 1B.

Referring now to the drawings, FIGS. 1A-1C illustrate aspects of wire bonding machines, and ultrasonic transducers, which are useful to explain various embodiments of the invention. For example, an ultrasonic transducer 100 shown in FIGS. 1A-1C may include a processed area having a changed condition at the surface of the transducer body (e.g., see the exemplary processed areas illustrated in FIGS. 2A-2B, FIGS. 3A-3B, and FIGS. 4A-4B).

As shown in FIG. 1A, a wire bonding machine 150 includes a bond head assembly 162, and an ultrasonic transducer 100 carried by bond head assembly 162. Ultrasonic transducer 100 includes a transducer body (e.g., see transducer body 100' in FIG. 1B), wherein at least a portion of a surface of the transducer body includes a processed area (e.g., see FIGS. 2A-2B, FIGS. 3A-3B, and FIGS. 4A-4B). The processed area has a changed condition at the surface of the transducer body.

Ultrasonic transducer 100 carries a wire bonding tool 108 for bonding wire portions (of a wire 160) to a workpiece 156. In the illustrated embodiment in FIG. 1A, workpiece 156 includes a semiconductor die 158 mounted on a substrate 154. Workpiece 156 is supported by a support structure 152 of wire bonding machine 150. As will be appreciated by those skilled in the art, wire bonding tool 108 (carried by bond head assembly 162) is moveable along a plurality of axes of wire bonding machine 150 to perform wire bonding operations. For example, wire bonding tool 108 is moved along an x-axis and a y-axis of wire bonding machine 150 through movement of bond head assembly 162, and wire bonding tool 108 is moved along a z-axis of wire bonding machine 150 through a z-axis motion system (not shown).

Ultrasonic transducer 100 provides ultrasonic scrub at a working end 108a of wire bonding tool 108 (also known as the tip portion of wire bonding tool 108) for bonding portions of wire 160 to workpiece 156. In FIG. 1A, a free air ball 160a (i.e., a portion of wire 160) is seated at working end 108a of wire bonding tool 108. Free air ball 160a will be bonded to workpiece 156 in connection with a wire bonding operation.

FIG. 1B-1C are more detailed perspective views of an example ultrasonic transducer 100 from FIG. 1A. Ultrasonic transducer 100 includes a transducer body 100'. Transducer body 100' includes mounting structures 102a and 102b used to mount ultrasonic transducer 100 to a bond head assembly of a wire bonding machine (e.g., see bond head assembly 162 in FIG. 1A). Piezoelectric crystals 104 are provided in a cavity 116 defined by ultrasonic transducer 100 (where cavity 116 is shown in FIGS. 2A-2B, FIGS. 3A-3B, and FIGS. 4A-4B), where piezoelectric crystals 104 provide ultrasonic energy to ultrasonic transducer 100 via the application of electrical energy to electrodes 106a and 106b. This ultrasonic energy is transmitted to wire bonding tool 108 which is used in wire bonding operations.

Transducer body 100' defines an aperture 112 configured to receive wire bonding tool 108. Transducer body 100' also defines a second aperture 110a configured to receive a fastener 110 for tightening aperture 112 during engagement with wire bonding tool 108. For example, fastener 110 may be a screw or another threaded fastener and is configured to be engaged with threads 110a1 of second aperture 110a. That is, wire bonding tool 108 is secured in aperture 112 by engaging fastener 110 in second aperture 110a using integral tool clamp 114 (e.g., a split clamp). More specifically, when fastener 110 is threaded through second aperture 110a, integral tool clamp 114 is compressed thereby causing aperture 112 to shrink. When aperture 112 shrinks, bearing surfaces 112a1 move inward radially which secures wire bonding tool 108 in aperture 112.

FIGS. 1A-1C illustrate exemplary features of wire bonding machine 150 including ultrasonic transducer 100. It is understood that various of these features may be altered within the scope of the invention. An exemplary feature according to aspects of the invention is that at least a portion of a surface of the transducer body includes a processed area. The processed area has a changed condition (e.g., wherein the changed condition may be configured to reduce galling and/or to reduce wear at the processed area). FIGS. 2A-2B, FIGS. 3A-3B, and FIGS. 4A-4B illustrate various examples of ultrasonic transducer 100 (labelled as ultrasonic transducer 100a in FIG. 2A, ultrasonic transducer 100b in FIG. 3A, and ultrasonic transducer 100c in FIG. 4A) with different processed areas having a changed condition. Of course, the invention is not limited to the examples shown in FIGS. 2A-2B, FIGS. 3A-3B, and FIGS. 4A-4B.

Figure 2A:
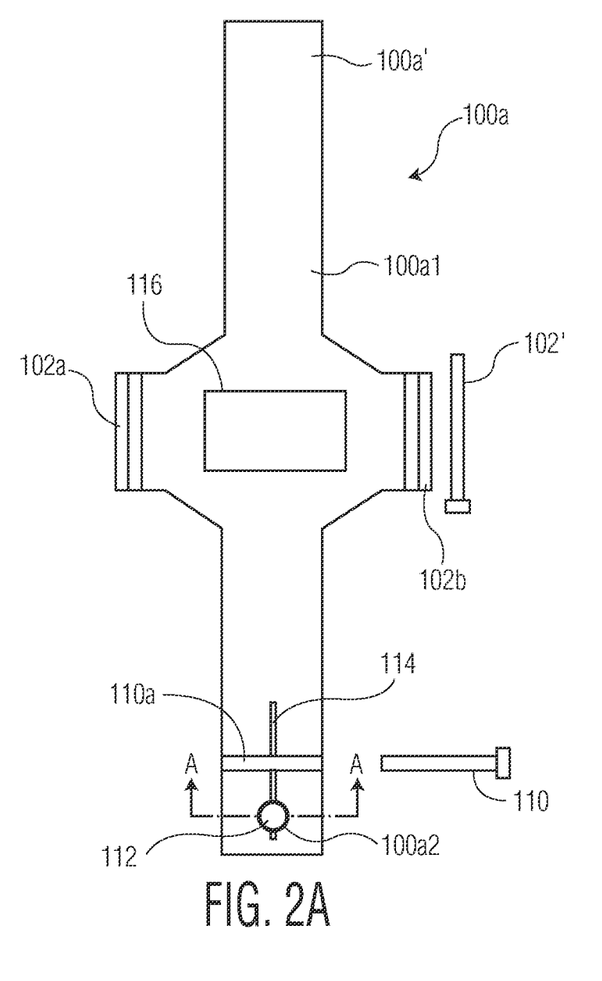
FIGS. 2A-2B, FIGS. 3A-3B, and FIGS. 4A-4B are top block diagram views, with partial side sectional views, of various ultrasonic transducers in accordance with various exemplary embodiments of the invention.
Figure 2B:
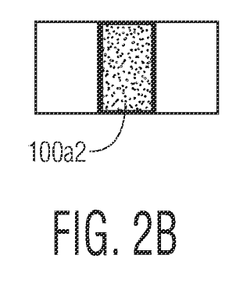

Referring now to FIG. 2A, ultrasonic transducer 100a (an example of transducer 100 shown in FIGS. 1A-1C) includes transducer body 100a'. Transducer body 100a' defines aperture 112, second aperture 110a, cavity 116, and integral tool clamp 114. An example fastener 102' is shown for engagement with each of mounting structures 102a, 102b for mounting of ultrasonic transducer 100a to a bond head assembly. Transducer body 100a' includes a surface 100a1 (i.e., an exterior surface). As provided above, at least a portion of surface 100a1 includes a processed area. In the example shown in FIG. 2A, the processed area is an area 100a2 defining aperture 112 configured to receive a wire bonding tool. FIG. 2B illustrates section A-A, which is a cross-section of area 100a2.

Figure 3A:
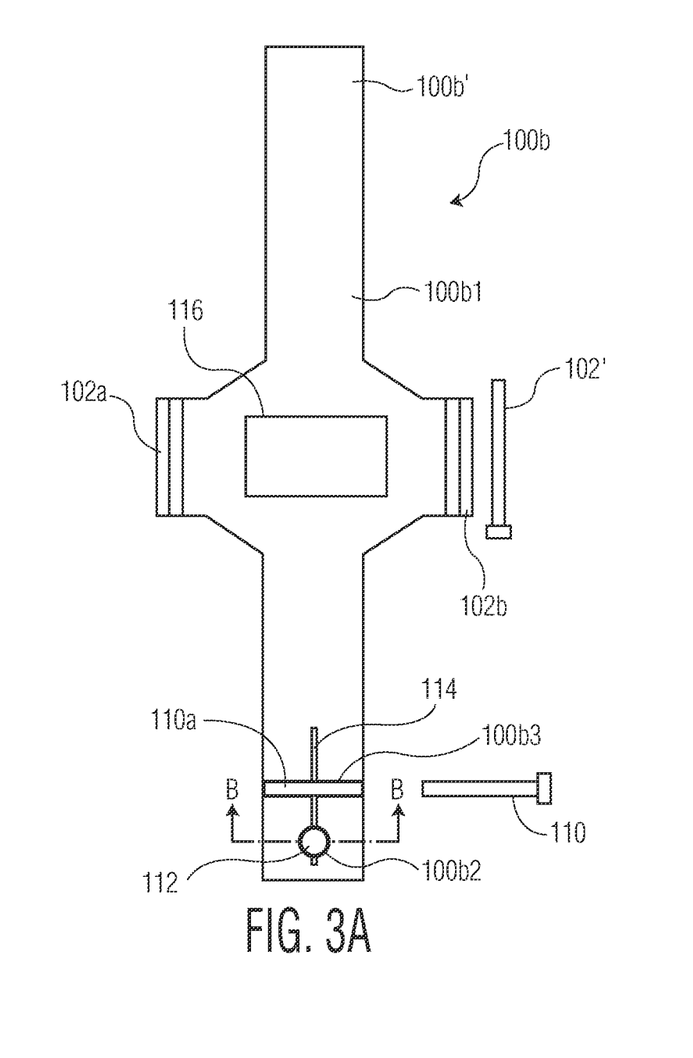
Figure 3B:
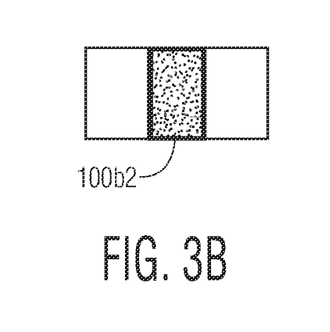

Referring now to FIG. 3A, ultrasonic transducer 100b (another example of ultrasonic transducer 100 shown in FIGS. 1A-1C) includes transducer body 100b'. Transducer body 100b' defines aperture 112, second aperture 110a, cavity 116, and integral tool clamp 114. An example fastener 102' is shown for engagement with each of mounting structures 102a, 102b for mounting of ultrasonic transducer 100a to a bond head assembly. Transducer body 100b' includes a surface 100b1 (i.e., an exterior surface). As provided above, at least a portion of surface 100b1 includes a processed area. In the example shown in FIG. 3A, the processed area includes (i) an area 100b2 defining aperture 112 configured to receive a wire bonding tool and (ii) an area 100b3 defining another aperture 110a (sometimes referred to herein as a second aperture configured to receive fastener 110 for tightening aperture 112 during engagement with a wire bonding tool). FIG. 3B illustrates section B-B, which is a cross-section of area 100b2.

Figure 4A:
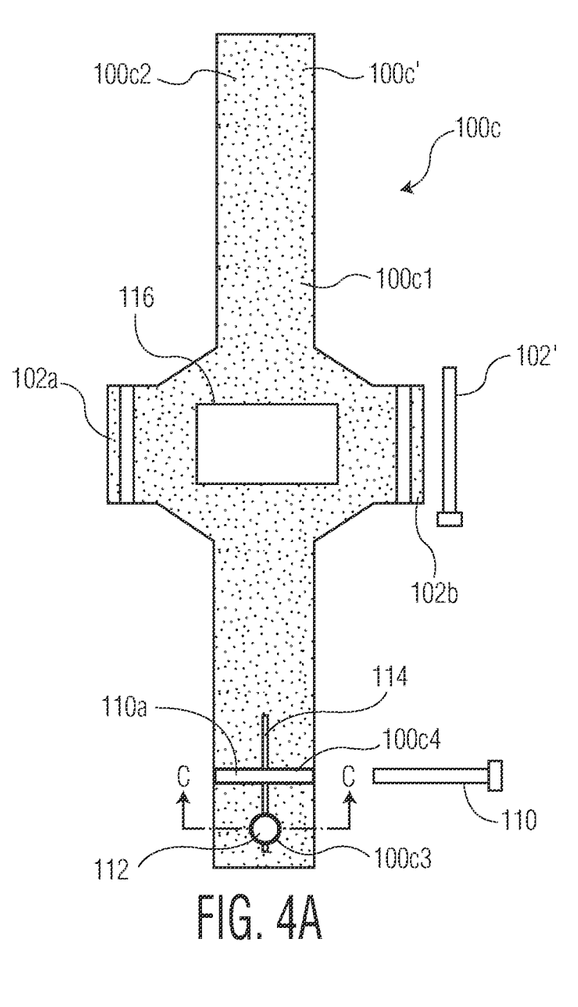
Figure 4B:
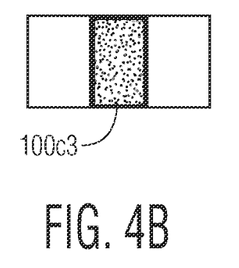

Referring now to FIG. 4A, ultrasonic transducer 100c (yet another example of ultrasonic transducer 100 shown in FIGS. 1A-1C) includes transducer body 100c'. Transducer body 100c' defines aperture 112, second aperture 110a, cavity 116, and integral tool clamp 114. An example fastener 102' is shown for engagement with each of mounting structures 102a, 102b for mounting of ultrasonic transducer 100a to a bond head assembly. Transducer body 100c' includes a surface 100c1 (i.e., an exterior surface). As provided above, at least a portion of surface 100c1 includes a processed area. In the example shown in FIG. 4A, the processed area includes an exterior surface of transducer body 100c, and is labelled as processed area 100c2. Processed area 100c2 in FIG. 4A also includes (i) an area 100c3 defining aperture 112 configured to receive a wire bonding tool, (ii) an area 100c4 defining another aperture 110a (sometimes referred to herein as a second aperture configured to receive fastener 110 for tightening aperture 112 during engagement with a wire bonding tool). FIG. 4B illustrates section C-C, which is a cross-section of area 100c3.

As referenced above, the processed area includes a changed condition at the surface of the transducer body. This applies to any of the processed areas according to any embodiment of the invention. For example, the processed area 100a2 shown in FIGS. 2A-2B, or the processed areas 100b2 and 100b3 shown in FIGS. 3A-3B, or the processed area 100c2 shown in FIGS. 4A-4B—all include a changed condition at the surface of the transducer body. For example, the changed condition may be configured to reduce wear and/or galling at the area of the transducer body defining the aperture 112.

The changed condition may include a coating applied at the processed area. Examples of the coating material include at least one of titanium nitride, diamond-like carbon, flash chrome, tungsten disulfide, titanium aluminum nitride, and composite diamond coating. Exemplary ranges for a thickness of the coating include (i) between 1 μm and 10 μm, and between 1 μm and 5 μm.

The changed condition may include a passivated condition (e.g., an anodized condition) at the processed area.

Figure 5A:
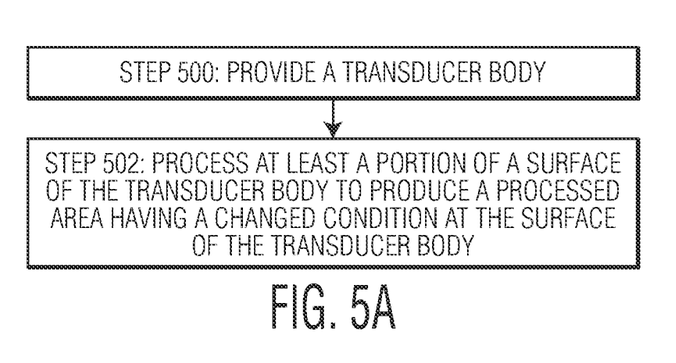
FIGS. 5A-5C are flow diagrams illustrating various methods of providing an ultrasonic transducer system in accordance with various exemplary embodiments of the invention.
Figure 5B:
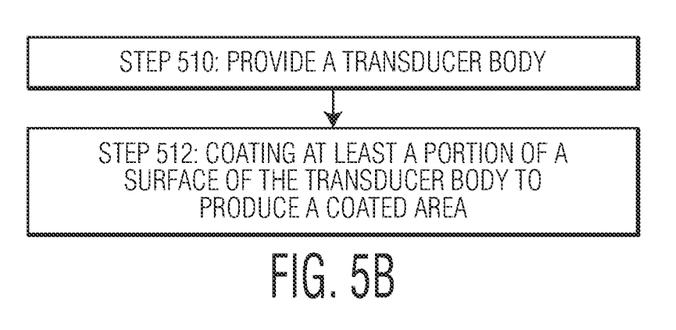
Figure 5C:
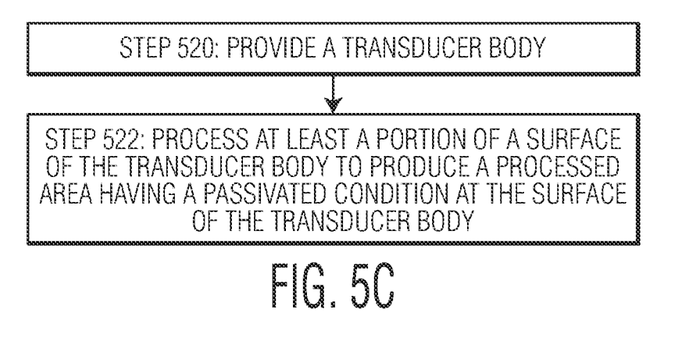

FIGS. 5A-5C are flow diagrams illustrating exemplary methods of providing an ultrasonic transducer in accordance with the invention. As is understood by those skilled in the art, certain steps included in the flow diagrams may be omitted; certain additional steps may be added; and the order of the steps may be altered from the order illustrated—all within the scope of the invention.

Referring now to FIG. 5A, at Step 500 a transducer body is provided. At Step 502, at least a portion of a surface of the transducer body is processed to produce a processed area. The processed area has a changed condition at the surface of the transducer body.

Referring now to FIG. 5B, at Step 510 a transducer body is provided. At Step 512, at least a portion of a surface of the transducer body is coated to produce a coated area (i.e., the processed area is a coated area in this example). The coating may be applied using any of a number of techniques such as spraying, plasma vapor deposition (PVD), chemical vapor deposition (CVD), etc. If the coating it not applied to the entire exterior surface of the transducer body, masking (or other techniques for selective coating) may be utilized.

Referring now to FIG. 5C, at Step 520 a transducer body is provided. At Step 522, at least a portion of a surface of the transducer body is processed to produce a processed area. The processed area has a passivated condition (e.g., an anodized condition) at the surface of the transducer body. For example, an electrolytic reaction may be performed at the surface to provide the passivated condition. Such a passivated condition may be considered to, for example: provide a protective oxide layer at the surface; to increase the thickness of the natural oxide layer at the surface; to produce a chemical reaction by consuming a small portion of material at the surface; etc.

Although the invention has been described primarily with respect to ultrasonic transducers for use in connection with wire bonding machines, it is not limited thereto. The teachings of the invention may be applicable to various applications of ultrasonic transducers outside of wire bonding including other applications in the semiconductor industry (e.g., flip chip bonding, wafer level bonding, etc.), and applications outside of the semiconductor industry. Further, the work tools carried by the ultrasonic transducer are not limited to wire bonding tools; other types of work tools are contemplated.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An ultrasonic transducer comprising:
a transducer body, the transducer body defining an aperture configured to receive a wire bonding tool, wherein an area of the transducer body defining the aperture is coated with a coating to reduce wear at the area.

2. The ultrasonic transducer of claim 1 wherein the transducer body defines a second aperture configured to receive a fastener for tightening the aperture during engagement with the wire bonding tool, another area of the transducer body defining the second aperture also being coated with the coating to reduce wear at the another area.

3. The ultrasonic transducer of claim 1 wherein the coating is configured to reduce galling at the area of the transducer body defining the aperture.

4. The ultrasonic transducer of claim 1 wherein an exterior surface of the transducer body also includes the coating.

5. The ultrasonic transducer of claim 1 wherein the coating has a thickness of between 1 µm and 10 µm.

6. The ultrasonic transducer of claim 1 wherein the coating includes at least one of titanium nitride, diamond-like carbon, flash chrome, tungsten disulfide, titanium aluminum nitride, and composite diamond coating.

7. The ultrasonic transducer of claim 1 wherein the coated area has a hardness greater than 90 HRC.

8. The ultrasonic transducer of claim 1 wherein the coated area has a coefficient of friction of less than 0.2.

9. The ultrasonic transducer of claim 1, the coating having a thickness of between 1 µm and 5 µm.

10. The ultrasonic transducer of claim 9 wherein the coating includes at least one of titanium nitride, diamond-like carbon, flash chrome, tungsten disulfide, titanium aluminum nitride, and composite diamond coating.

11. A wire bonding machine comprising:
a bond head assembly; and
an ultrasonic transducer carried by the bond head assembly, the ultrasonic transducer including a transducer body, the transducer body defining an aperture configured to receive a wire bonding tool, wherein an area of the transducer body defining the aperture is coated with a coating to reduce wear at the area.

12. The wire bonding machine of claim 11 wherein the transducer body defines a second aperture configured to receive a fastener for tightening the aperture during engagement with the wire bonding tool, another area of the transducer body defining the second aperture also being coated with the coating to reduce wear at the another area.

13. The wire bonding machine of claim 11, the coating having a thickness of between 1 µm and 5 µm.

14. The wire bonding machine of claim 13 wherein the coating includes at least one of titanium nitride, diamond-like carbon, flash chrome, tungsten disulfide, titanium aluminum nitride, and composite diamond coating.

15. A method of providing an ultrasonic transducer, the method comprising the steps of:
(a) providing a transducer body, the transducer body defining an aperture configured to receive a wire bonding tool; and
(b) applying a coating to an area of the transducer body defining the aperture to reduce wear at the area.

16. The method of claim 15 wherein the transducer body provided in step (a) defines a second aperture configured to receive a fastener for tightening the aperture during engagement with the wire bonding tool, and step (b) includes applying the coating to another area of the transducer body defining the second aperture.

17. The method of claim 15, the coating having a thickness of between 1 µm and 10 µm.

18. The method of claim 17 wherein the coating includes at least one of titanium nitride, diamond-like carbon, flash chrome, tungsten disulfide, titanium aluminum nitride, and composite diamond coating.

* * * * *